(12) United States Patent
Filicori

(10) Patent No.: US 7,964,562 B2
(45) Date of Patent: Jun. 21, 2011

(54) UNITARY COMBINATIONS OF FSH AND HCG

(75) Inventor: Marco Filicori, Bologna (IT)

(73) Assignee: Ferring B.V., Hoofddorp (NL)

( * ) Notice: Subject to any disclaimer, the term of this patent is extended or adjusted under 35 U.S.C. 154(b) by 0 days.

(21) Appl. No.: 11/979,265

(22) Filed: Oct. 31, 2007

(65) Prior Publication Data

US 2008/0108571 A1 May 8, 2008

Related U.S. Application Data

(63) Continuation of application No. 10/559,610, filed as application No. PCT/IB2004/001813 on Jun. 2, 2004, which is a continuation-in-part of application No. 10/452,926, filed on Jun. 3, 2003, now abandoned.

(51) Int. Cl.
*A61K 38/24* (2006.01)
*C07K 14/59* (2006.01)

(52) U.S. Cl. .......... 514/9.7; 514/9.8; 514/9.9; 514/10.1; 530/398

(58) Field of Classification Search .................. None
See application file for complete search history.

(56) References Cited

U.S. PATENT DOCUMENTS

| | | | |
|---|---|---|---|
| 5,656,597 | A | 8/1997 | Skrabanja et al. |
| 5,929,028 | A | 7/1999 | Skrabanja et al. |
| 2003/0181361 | A1 | 9/2003 | Sharma et al. |
| 2004/0142887 | A1 | 7/2004 | Cui et al. |
| 2004/0248784 | A1 | 12/2004 | Filicori |
| 2006/0135421 | A1 | 6/2006 | Filicori |
| 2006/0229288 | A1 | 10/2006 | Palmer et al. |
| 2008/0119394 | A1 | 5/2008 | Filicori |

FOREIGN PATENT DOCUMENTS

| | | |
|---|---|---|
| EP | 1 364 658 A | 11/2003 |
| WO | WO 00/67778 | * 11/2000 |
| WO | WO-00/67778 A | 11/2000 |
| WO | WO-03/022302 A | 3/2003 |
| WO | WO-03/022303 A | 3/2003 |

OTHER PUBLICATIONS

Filicori et al. Low-dose human chorionic gonadotropin therapy can improve sensitivity to exogenous follicle-stimulating hormone in patients with secondary amenorrhea. Fertility and Sterility. vol. 72, No. 6, (Dec. 1999).*

Filicori et al., "Stimulation and Growth of antral ovarian fillicles by selective LH activity administration in women," *Journal of Clinical Endocrinology and Metabolism*, Mar. 2002, pp. 1156-1161.

Filicori et al., "Luteinizing hormone activity supplementation enhances follicle-stimulating hormone efficacy and improves ovulation induction outcome," *Journal of Clinical Endocrinology and Metabolism*, vol. 84, No. 8, Aug. 1999, pp. 2659-2663.

Thompson et al., "Gonadotrophin requirements of the developing follicle," *Fertility and Sterility*, vol. 63, No. 2, Feb. 1995, pp. 273-276.

Ascoli, "Characterization of Several Clonal Lines of Cultured Leydig Tumor Cells: Gonadotropin Receptors and Steroidogenic Responses," Endocrinology, 1981, pp. 88-95, vol. 108, No. 1, The Endocrine Society.

Campbell et al., "Examination of the Relative Role of FSH and LH in the Mechanism of Ovulatory Follicle Selection in Sheep," Journal of Reproductive and Fertility, 1999, pp. 355-367, vol. 117, Journals of Reproduction and Fertility Ltd.

Chang et al., "Recombinant Human Chorionic Gonadotropin (rhCG) in Assisted Reproductive Technology: Results of a Clinical Trial Comparing Two Doses of rhCG (Ovidrel$^R$) to Urinary hCG (Profasi$^R$) for Induction of Final Follicular Maturation in in vitro Fertilization-Embryo Transfer," Fertility and Sterility, Jul. 2001, pp. 67-74, vol. 76, No. 1, American Society for Reproductive Medicine.

Chappel et al., "Biosynthesis and Secretion of Follicle-Stimulating Hormone," Endocrine Reviews, 1983, pp. 179-211, vol. 4, No. 2, The Endocrine Society.

Clasesson L., et al., "Crystalline Human Chorionic Gonadotrophin and its Biological Action," ACTA Endocrinologica, 1948, vol. I, pp. 1-18.

Dighe et al., "Use of a- and /3-Subunit Specific Antibodies in Studying Interaction of hCG with Leydig Cell Receptors", Archives of Biochemistry and Biophysics, Sep. 1983, pp. 490-499, vol. 225, No. 2, Academic Press, Inc.

Fevold, H. L. et al., "Studies in the Physical Chemistry of the Anterior Pituitary Hormones," Endocrinology, May 1940, vol. 26, pp. 999-1004.

Filicori et al., "Modulation of Folliculogenesis and Steroidogenesis in Women by Graded Menotrophin Administration," Human Reproduction, 2002, pp. 2009-2015, vol. 17, No. 8, European Society of Human J Reproduction and Embryology.

Filicori et al., "The Use of LH Activity to Drive Folliculogenesis: Exploring Uncharted Territories in Ovulation Induction," Human Reproduction Update, 2002, pp. 543-557, vol. 8, No. 6, European Society of Human Reproduction and Embryology.

Filicori, "Use of Luteinizing Hormone in the Treatment of Infertility: Time for Reassessment?," Fertility and Sterility, Feb. 2003, pp. 253-255, vol. 79, No. 2, American Society for Reproductive Medicine.

(Continued)

*Primary Examiner* — Marianne P Allen
*Assistant Examiner* — Regina M DeBerry
(74) *Attorney, Agent, or Firm* — Foley & Lardner LLP

(57) ABSTRACT

A novel ovulatory induction paradigm entails administration of hCG in combination with FSH during all stages of treatment, where the ratio of FSH to hCG is adjusted to optimize ovulatory stimulation and minimize complications. The use of compositions characterized by various FSH:hCG ratios enables the practitioner readily to tailor the treatment regimen and accommodate different therapeutic goals as well as individual patient responses to gonadotropin administration.

7 Claims, 2 Drawing Sheets

OTHER PUBLICATIONS

Fraenkel-Conrat et al., "Purification of Follicle-Stimulating Hormone (FSH) of the Anterior Pituitary," Proc. Soc. Exp. Biol. Med., 1940, vol. 45, pp. 627-630.

Gordon et al., Abstracts of the 13th Annual Meeting of the ESHRE, 1997, pp. 52-54, Edinburgh.

Greep, B. F., et al., "Separation in Nearly Pure Form of Luteinizing (interstitial Cell-Stimulating) and Follicle-Stimulating (Gametogenic) Hormones of the Pituitary Gland," J. Biol. Chem., 1940, vol. 133, pp. 289-291.

Gupta et al., "Hyperexpression of Biologically Active Human Chorionic Gonadotropin Using the Methylotropic Yeast," Pichia Pinions, Journal of Molecular Endocrinology, 1999, pp. 273-283, vol. 22, Society of Endocrinology.

Hillier et al., 'Follicular Oestrogen Synthesis: The Two-Cell, Two-Gonadotrophin' Model Revisited, Molecular and Cellular Endocrinology, 1994, pp. 51-54, vol. 100, Elsevier Science Ireland Ltd.

Katzman, P.A., et al., "The Preparation of Chorionic Gonadotropin by Chromatographic Adsorption," J. Biol. Chem., 1943, vol. 148, pp. 501-507.

Keene et al., "Expression of Biologically Active Human Follitropin in Chinese Hamster Ovary Cells," The Journal of Biological Chemistry, Mar. 25, 1989, pp. 4769-4775, vol. 264, No. 9, The American Society for Biochemistry and Molecular Biology, Inc.

Li, et al., "Isolation of Pituitary Follicle Stimulating Hormone (FSH)," Science, 1949, vol. 109, pp. 445-446.

Martin et al., "ART: Ovarian Stimulation," Fertility & Sterility, Oct. 14, 2002, p. S19.

McShan, W.H., et al., "The Preparation and Properties of Pituitary Follicle-Stimulating Fractions Made by Trypsin Disgestion," J. Biol. Chem., 1940, vol. 135, pp. 473-482.

Remington's Pharmaceutical Sciences, 15th Ed. (Mark Publishing Co. 1975), pp. 1405-1412 and 1461-1487.

Shoham, "The Clinical Therapeutic Window for Luteinizing Hormone in Controlled Ovarian Stimulation," Fertility and Sterility, Jun. 2002, pp. 1170-1177, vol. 77, No. 6, American Society for Reproductive Medicine.

Snyder et al., "Characterization of Human LH Isohormones From Fresh Pituitary Tissue," Molecular and Cellular Endocrinology, 1987, pp. 115-121, vol. 54, Elsevier Scientific Publishers Ireland Ltd.

Van Hell, H., et at., "Effects of Human Menopausal Gonadotrophin Preparations in Different Bioassay Methods," ACTA Endocrinologica, 1964, vol. 47, No. 3, pp. 407-418.

Warne et al., "Induction of Ovulation in World Health Organization Group II Anovulatory Women Undergoing Follicular Stimulation with Recombinant Human Follicle-Stimulating Hormone: A Comparison of Recombinant Human Chorionic Gonadotropin (rhCG) and Urinary hCG," Fertility and Sterility, Jun. 2001, pp. 1111-1118, vol. 75, No. 6, American Society for Reproductive Medicine.

Zondek and Aschheim, Klin, Wochenschr, 1928, vol. 7, pp. 931-932. Abstracts of the 13th Annual Meeting of the ESHRE, 1997, pp. 52-54, Edinburgh.

"Induction of ovulation in World Health Organization group II anovulatory women undergoing follicular stimulation with recombinant human follicle-stimulating hormone: a comparison of recombinant human chorionic gonadotropin (rhCG) and urinary hCG", Fertility and Sterility, Jun. 2001, pp. 1111-1118, vol. 75, No. 6, American Society for Reproductive Medicine.

Bremner, et al., "Follicle-stimulating Hormone and Human Spermatogenesis," The Journal of Clinical Investigation, vol. 68, Oct. 1981, pp. 1044-1052.

Chow, B. F., et al., "Separation in Nearly Pure Form of Luteinizing (interstitial Cell-Stimulating) and Follicle-Stimulating (Gametogenic) Hormones of the Pituitary Gland", J. Biol. Chem., vol. 133, pp. 289-291 (1940).

Filicori et al., "Stimulation and Growth of Antral Ovarian Follicles by Selective LH Activity Administration in Women", The Journal of Clinical Endocrinology & Metabolism, 2002, pp. 1156-1161, vol. 87, No. 3, The Endocrine Society.

Filicori, Use of luteinizing hormone in the treatment of infertility: time for reassessment?, Fertility and Sterility, Feb. 2003, pp. 253-255, vol. 79, No. 2, American Society for Reproductive Medicine.

Thompson et al., "Gonadotrophin Requirements of the Developing Follicle," Fertility and Sterility, vol. 63, No. 2, Feb. 1995, pp. 273-276.

Butler, "hCG-Mass units, molar conversions, and the standardization of biologic units," *Fertility & Sterility*, vol. 80, No. 6, p. 1533, Dec. 2003.

* cited by examiner

FIGURE 1A

| | FSH (IU) | | | | |
|---|---|---|---|---|---|
| | 50 | 75 | 100 | 150 | 200 |
| | | | | | |
| | 1 | 1 | 1 | 1 | 1 |
| | 5 | 5 | 5 | 5 | 5 |
| | 10 | 10 | 10 | 10 | 10 |
| | 25 | 25 | 25 | 25 | 25 |
| hCG (IU) | 50 | 50 | 50 | 50 | 50 |
| | 75 | 75 | 75 | 75 | 75 |
| | 100 | 100 | 100 | 100 | 100 |
| | 200 | 200 | 200 | 200 | 200 |
| | 300 | 300 | 300 | 300 | 300 |
| | 400 | 400 | 400 | 400 | 400 |

FIGURE 1B

| | FSH (IU) | | | | |
|---|---|---|---|---|---|
| | 50 | 75 | 100 | 150 | 200 |
| | | | | | |
| | 0.04 | 0.04 | 0.04 | 0.04 | 0.04 |
| | 0.2 | 0.2 | 0.2 | 0.2 | 0.2 |
| | 0.4 | 0.4 | 0.4 | 0.4 | 0.4 |
| | 1 | 1 | 1 | 1 | 1 |
| Recombinant hCG ($\mu$g) | 2 | 2 | 2 | 2 | 2 |
| | 3 | 3 | 3 | 3 | 3 |
| | 4 | 4 | 4 | 4 | 4 |
| | 8 | 8 | 8 | 8 | 8 |
| | 12 | 12 | 12 | 12 | 12 |
| | 16 | 16 | 16 | 16 | 16 |

UNITARY COMBINATIONS OF FSH AND HCG

This application is a continuation of U.S. application Ser. No. 10/559,610 filed Jan. 31, 2006, as the U.S. National Stage of PCT/IB2004/001813, filed Jun. 2, 2004, which is a continuation-in-part of U.S. application Ser. No. 10/452,926, filed Jun. 3, 2003.

FIELD OF THE INVENTION

The present invention relates to novel gonadotropin formulations. More specifically, the invention relates to pharmaceutical formulations, useful for ovarian stimulation, in which both follicle stimulating hormone (FSH) and human chorionic gonadotropin (hCG) are present.

BACKGROUND OF THE INVENTION

Assisted reproduction technology (ART) procedures typically require treatment with exogenous gonadotropins to stimulate growth and maturation of the ovarian follicles. When gonadotropins are used to treat anovulatory females, the goal is to replicate the normal menstrual cycle, when a single, dominant follicle matures prior to induction of ovulation. In contrast, for women undergoing in vitro fertilization (IVF), controlled ovarian stimulation (COS) is employed to stimulate the growth and maturation of several ovarian follicles, yielding multiple oocytes, which then are retrieved for use in the IVF procedure.

Despite recent advances in ART, ovarian stimulation through exogenous gonadotropins is not uniformly successful due, in part, to varying individual responses to treatment with gonadotropins. This variability complicates patient management and can result in multiple births and potentially life-threatening complications.

Gonadotropins are secreted by the pituitary gland under the control of hypothalamic gonadotropin-releasing hormone (GnRH). Follicle stimulating hormone (FSH) and luteinizing hormone (LH) are the pituitary hormones essential for follicular maturation (folliculogenesis) and luteinization. FSH is required for follicular recruitment (i.e., the early growth of ovarian follicles) at the beginning of the spontaneous menstrual cycle, and it also supports mid- and late-stage folliculogenesis.

FSH is administered therapeutically to induce folliculogenesis in anovulatory women and women undergoing COS. In traditional ovulatory stimulation methods, FSH is administered throughout treatment until the time that oocytes are retrieved. This continued stimulation by FSH can cause multiple conceptions and the potentially fatal condition, ovarian hyperstimulation syndrome (OHSS). Decreasing the dosage of FSH can reduce the risk of OHSS, but low FSH dosages yield inadequate follicle quantities and thus lower the chances of success in assisted reproduction.

LH functions during all stages of a normal menstrual cycle. LH stimulates the theca cells of the follicle to produce the androgen substrate which is converted into estrogen by the aromatase system in the granulosa cells. During the late stages of follicle maturation, approximately 5 to 7 days before ovulation, large ovarian follicles begin to express LH receptors in granulosa cells, which render those follicles responsive to LH for continued maturation and development. Hillier et al., *Mol. Cell Endocrinol.* 100:51 (1994), Campbell et al. *J. Reprod. Fertil.* 117:244 (1999). Next, a mid-cycle surge of LH triggers the final stage of follicular maturation and ovulation in a normal menstrual cycle. Ovulation follows the mid-cycle LH surge within 24 to 48 hours. Finally, in the second part of the menstrual cycle, the luteal phase, LH stimulated production of estrogen and progesterone in the corpus luteum of the ovary prepares the uterus for implantation and pregnancy.

In ovarian stimulation protocols, hCG can serve as a source of LH activity because hCG and LH act through the same receptor. Filicori et al. *Human Reprod.* 17:2009 (2002a); Martin et al., *Fertil. Steril.* 76: O-49 (2002). Relative to LH, hCG has a longer half-life and, hence, is more potent than LH, although the literature tends to treat hCG and LH as fungible. Indeed, the scientific literature generally does not mention determining the source of LH activity in naturally-derived gonadotropin preparations. But see Filicori et al., *Human Reprod. Update* 8: 543, 552 (2002b) ("likely hCG content of [a particular] hMG preparation" extrapolated to be "~5 IU per ampoule," such that, "of the 75 IU of LH potency contained in this hMG preparation, about 30 IU are provided by hCG").

The literature discloses using LH activity or low doses of hCG in combination with FSH throughout ovulatory stimulation, but guidance regarding effective amounts and timing of LH activity supplementation is lacking. For example, the abstract of Martin et al., *Fertil. Steril.* 76: O-49 (2002), discloses administering 2.5 µg recombinant hCG daily (maintaining serum hCG levels from 1-3 mIU/mL) during ovulatory stimulation. Gordon et al. disclose administering 75 IU FSH with 0, 1, 25, and 75 IU LH activity. *Human Reprod.* 12 (Suppl. 1): 52 (1997a); ibid.: 53 (1997b).

Published studies disclose administering LH activity, throughout stimulation, at FSH to LH ratios of 150:0, 150:37.5, 150:75, and 150:150. Filicori et al. (2002a). Further, the literature documents supplementing FSH stimulation with 50 IU hCG/day (Filicori et al., *J. Clin. Endocrinol. & Metabol.* 84: 2659 (1999)), and protocols in which 150 IU FSH is administered for 7 days, followed by treatment with FSH-to-hCG ratios of 150:0, 50:50, 25:100, and 0:200 (ibid. 87:1156 (2002c)).

The literature documents other compositions that contain both FSH and LH activity, as well as use of FSH in combination with LH activity. For example, PCT application WO 00/67778, published Nov. 16, 2000, is directed to using LH or an equivalent amount of hCG in combination with FSH to induce folliculogenesis in anovulatory women. More particularly, the '778 application discloses administering LH or "a biologically-active analogue thereof" in doses of 100 to 1500 IU per day (page 4, lines 26-29) and in FSH:LH ratios that range from 1:1.5 to 1:20 (id., lines 16-18).

U.S. Pat. No. 5,929,028 is directed to liquid formulations that contain one or more natural or recombinant gonadotropins, including FSH, LH, and hCG. The '028 patent discusses naturally derived compositions of human menopausal gonadotropin (hMG), which have FSH and LH activities in a ratio of approximately 1:1, but mentions no ratio of FSH to LH activity other than the 1:1 ratio of commercial hMG preparations.

Additionally, there are commercial formulations that contain both FSH and LH. Human-derived preparations are available containing 75 IU FSH with 75 IU LH activity (Pergonal, Humegon, Menogon, Repronex, and Menopur) and 75 IU FSH with 25 or 35 IU LH activity (Normegon and Pergogreen).

It is conventional wisdom, however, that "excessive" LH levels, albeit ill-defined, result in follicular atresia, suppression of granulosa cell proliferation, and premature luteinization. See, generally, Filicori, *Fertil. Steril.* 79: 253 (2003). Although recent work suggests otherwise, a notion persists in the field that LH activity levels must be within a certain range, and that levels below or above an "LH ceiling" impair normal follicle development. Shoham, *Fertil. Steril.* 70: 1170 (2002).

In summary, there is published evidence that supplementing FSH with LH activity during ovulation induction reduces the duration of treatment and the amount of gonadotropin used to achieve proper follicle development. Filicori et al. (1999), (2002b). On the other hand, the belief persists that "high" LH activity levels negatively impacts follicle development.

That belief has guided the conventional ovarian-stimulation paradigm, which involves administration of FSH throughout controlled ovarian stimulation. Exogenous LH activity is deemed unnecessary and even detrimental during the early to middle stages of follicular development. Accordingly, the traditional means of ovarian stimulation entails treatment with FSH alone, typically at 75 IU/day. In this traditional protocol, LH activity is administered to induce ovulation only after the follicle reaches a certain stage of development. Only recently has LH activity been administered throughout treatment, and the optimal amount and timing of LH activity that is effective in this context remains controversial.

SUMMARY OF THE INVENTION

Conventional protocols of ovulation stimulation do not accommodate selective treatment regimens that optimize ovarian follicle development. Furthermore, available gonadotropic preparations are not easily adapted to different therapeutic goals. Thus, a need exists for compositions that combine FSH and hCG in varying ratios, thereby to enable the practitioner to tailor a gonadotropin treatment regimen to the needs of the individual patient. Methodology also is needed for using such compositions to stimulate folliculogenesis in anovulatory females and in the context of ART procedures.

To these ends, inter alia, the present invention provides pharmaceutical compositions that contain various amounts of FSH and hCG, as well as various FSH-to-hCG ratios, supplied in a single preparation. These compounds enable the practitioner to optimize ovulatory stimulation in flexible manner not possible with available preparations.

The present invention also comprehends an approach to inducing ovulation, by using compositions with varying FSH: hCG ratios. The inventive methodology allows for incremental adjustments in the ratio of FSH to hCG, as a function of the stage of folliculogenesis or of variation in patient response, resulting in safer and more successful ovulatory stimulation.

One embodiment of the invention is a pharmaceutical composition that consists essentially of FSH and hCG in a pharmaceutically acceptable carrier. According to the invention, the ratio of FSH to hCG in such a composition is conducive, upon administration of the composition, to folliculogenesis and to follicular maturation without ovarian hyperstimulation. In this regard, use of the phrase "consists essentially of" means that the composition, while possibly having other constituents, does not include any component that inhibits or otherwise detracts from the beneficial properties of the composition with respect to folliculogenesis or follicular maturation.

Another embodiment of the invention is an assemblage comprising a first vial and a second vial, each of said vials containing a pharmaceutical composition consisting essentially of FSH and hCG in a pharmaceutically acceptable carrier, wherein the ratio of FSH to hCG is conducive, upon administration of said composition, to folliculogenesis and follicular maturation without ovarian hyperstimulation. The ratio of FSH to hCG differs between the first vial and the second vial.

A further embodiment of the invention is a method of inducing ovulation, comprising: administering at least one pharmaceutical composition characterized by a ratio of FSH to human hCG that is selected from the group consisting of 50 IU FSH:1 IU hCG, 50 IU FSH:5 IU hCG, 50 IU FSH:10 IU hCG, 50 IU FSH:25 IU hCG, 50 IU FSH:75 IU hCG, 50 IU FSH:100 IU hCG, 50 IU FSH:200 IU hCG, 50 IU FSH:300 IU hCG, 50 IU FSH:400 IU hCG, 75 IU FSH:1 IU hCG, 75 IU FSH:5 IU hCG, 75 IU FSH:10 IU hCG, 75 IU FSH:25 IU hCG, 75 IU FSH:50 IU hCG, 75 IU FSH:75 IU hCG, 75 IU FSH:100 IU hCG, 75 IU FSH:200 IU hCG, 75 IU FSH:300 IU hCG, 75 IU FSH:400 IU hCG, 100 IU FSH:1 IU hCG, 100 IU FSH:5 IU hCG, 100 IU FSH:10 IU hCG, 100 IU FSH:25 IU hCG, 100 IU FSH:50 IU hCG, 100 IU FSH:75 IU hCG, 100 IU FSH:100 IU hCG, 100 IU FSH:200 IU hCG, 100 IU FSH:300 IU hCG, 100 IU FSH:400 IU hCG, 150 IU FSH:1 IU hCG, 150 IU FSH:5 IU hCG, 150 IU FSH:10 IU hCG, 150 IU FSH:25 IU hCG, 150 IU FSH:75 IU hCG, 150 IU FSH:100 IU hCG, 150 IU FSH:200 IU hCG, 150 IU FSH:300 IU hCG, 150 IU FSH:400 IU hCG, 200 IU FSH:1 IU hCG, 200 IU FSH:5 IU hCG, 200 IU FSH:10 IU hCG, 200 IU FSH:25 IU hCG, 200 IU FSH:50 IU hCG, 200 IU FSH:75 IU hCG, 200 IU FSH:100 IU hCG, 200 IU FSH:200 IU hCG, 200 IU FSH:300 IU hCG, and 200 IU FSH:400 IU hCG, monitoring serum hormone levels, follicle size and follicle number; and then inducing ovulation by administration of an hCG bolus.

Other features, objects, and advantages of the present invention are apparent in the detailed description that follows. It should be understood, however, that the detailed description, while indicating preferred embodiments of the invention, are given by way of illustration only, not limitation. Various changes and modifications within the spirit and scope of the invention will become apparent to those skilled in the art from the detailed description.

BRIEF DESCRIPTION OF THE DRAWINGS

FIG. 1 shows useful FSH-to-hCG ratio values, where FSH amount is expressed in international units (IU) and hCG amount is expressed in IU (FIG. 1A) and micrograms (FIG. 1B).

DETAILED DESCRIPTION OF THE PREFERRED EMBODIMENTS

Figure 2:
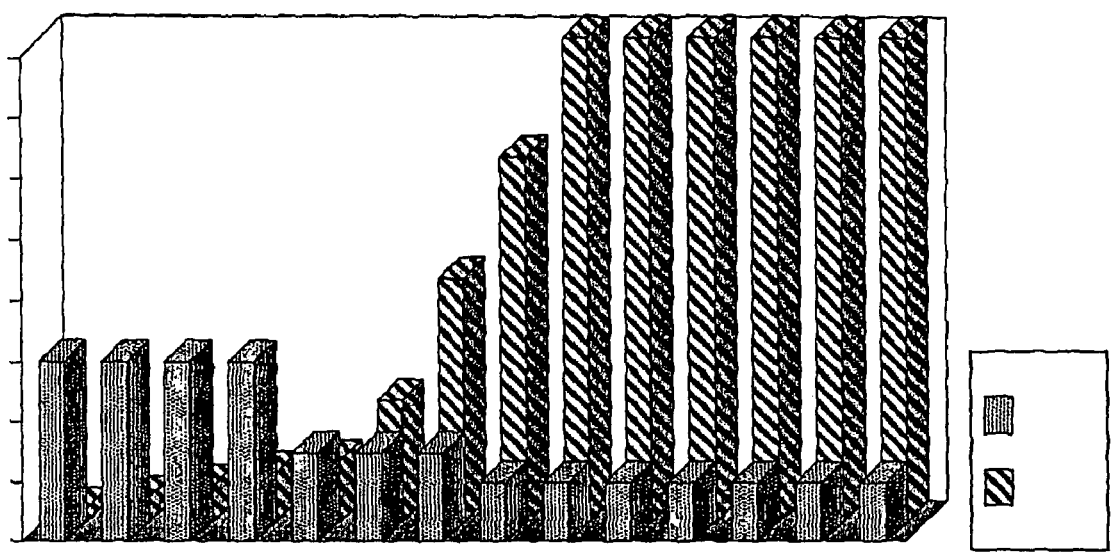
FIG. 2 is a bar graph that depicts a proposed treatment protocol according to the invention, using FSH:hCG compositions as described above.

The invention provides compositions and methods for a novel therapeutic paradigm, characterized by administration of hCG in combination with FSH during all stages of treatment and by an adjustment of the FSH-to-hCG ratio, to optimize ovulatory stimulation. This paradigm departs substantially from the conventional approach, where FSH is administered alone, typically at 75-300 IU/day, and a bolus of LH activity is administered mid-cycle to induce ovulation.

The invention provides pharmaceutical compositions with a wide range of FSH to hCG ratios. The compositions and methods of the invention enable the physician to easily tailor treatment to a given patient's situation, allowing the ratio of FSH to hCG to be fine-tuned based on different stages of folliculogenesis and varying patient response to gonadotropins. Further, having a range of therapeutic compositions available, including those with high levels of hCG, allows the physician to easily accommodate the therapeutic requirements of various ART procedures. This flexibility is not possible with current gonadotropic preparations.

Because the compositions of the invention have a broad range of FSH to hCG ratios, the invention can easily be used to stimulate folliculogenesis and ovulation in any ovulation induction and ART procedure including among others, treatment of anovulatory infertility, in-vitro fertilization (IVF), intracytoplasmic sperm injection (ICSI), gamete intrafallopian transfer (GIFT), zygote intrafallopian transfer (ZIFT), cryopreserved embryo transfer, intrauterine insemination (IUI), donor oocyte transfer, cryopreserved embryo transfer from donor oocytes, and ART cycles for host uterus transfer. The compositions and methods of the invention can also be used to treat anovulatory patients and patients with hypogonadotropic hypogonadism and the polycystic ovary syndrome.

The compositions of the invention employ hCG as a source of LH activity. hCG binds to LH receptors and exerts through them its biological actions; separate hCG receptors do not exist. Using hCG in accordance with the invention has significant advantages over the use of LH. For instance, human-derived hCG is less expensive than either human-derived or recombinant FSH. From a cost perspective, therefore, it is favorable to minimize the amount of FSH used during the stimulation protocol. Furthermore, the use of hCG in a pharmaceutical composition of the invention more physiologically and effectively supports the final stages of maturation of large and mature ovarian follicles during COS, increases ovarian and blood estrogen levels, improves oocyte and embryo quality, lowers the amount and duration of FSH administration, and reduces the risk of FSH-associated complications such as multiple conceptions and OHSS.

In summary, the compositions and methods of the invention empower treatment regimens that achieve higher rates of success, that decrease the risk of complications, that are easy to implement, and that are less costly than those of conventional practice.

Unless indicated otherwise, all technical and scientific terms are used in a manner that conforms to common technical usage. Generally, the nomenclature of this description and the described laboratory procedures are well known and commonly employed in the art. Standard techniques are used for recombinant nucleic acid methods, microbial culture, cell culture, tissue culture, transformation, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. Absent an indication to the contrary, the techniques and procedures in question are performed according to conventional methodology disclosed, for example, in Sambrook et al., MOLECULAR CLONING A LABORATORY MANUAL, 2d ed. (Cold Spring Harbor Laboratory Press, 1989), and CURRENT PROTOCOLS IN MOLECULAR BIOLOGY, John Wiley & Sons, 1989).

Unitary Combinations of FSH and hCG

The invention provides novel pharmaceutical compositions useful for inducing ovarian stimulation in a mammal. "Mammal" refers to a human, non-human primate, sheep, pig, cow, horse, donkey, mouse, rat, rabbit, guinea pig, dog, cat, or captive wild animal. Preferably, the mammal is a human.

The pharmaceutical compositions contain 50 to 200 IU FSH together with 1 to 400 IU human-derived hCG (see FIG. 1A). Preferably, the compositions contain FSH and hCG in the following ratios: 50 IU FSH:1 IU hCG, 50 IU FSH:5 IU hCG, 50 IU FSH:10 IU hCG, 50 IU FSH:25 IU hCG, 50 IU FSH:75 IU hCG, 50 IU FSH:100 IU hCG, 50 IU FSH:200 IU hCG, 50 IU FSH:300 IU hCG, 50 IU FSH:400 IU hCG, 75 IU FSH:1 IU hCG, 75 IU FSH:5 IU hCG, 75 IU FSH:10 IU hCG, 75 IU FSH:25 IU hCG, 75 IU FSH:50 IU hCG, 75 IU FSH:75 IU hCG, 75 IU FSH:100 IU hCG, 75 IU FSH:200 IU hCG, 75 IU FSH:300 IU hCG, 75 IU FSH:400 IU hCG, 100 IU FSH:1 IU hCG, 100 IU FSH:5 IU hCG, 100 IU FSH:10 IU hCG, 100 IU FSH:25 IU hCG, 100 IU FSH:50 IU hCG, 100 IU FSH:75 IU hCG, 100 IU FSH:100 IU hCG, 100 IU FSH:200 IU hCG, 100 IU FSH:300 IU hCG, 100 IU FSH:400 IU hCG, 150 IU FSH:1 IU hCG, 150 IU FSH:5 IU hCG, 150 IU FSH:10 IU hCG, 150 IU FSH:25 IU hCG, 150 IU FSH:75 IU hCG, 150 IU FSH:100 IU hCG, 150 IU FSH:200 IU hCG, 150 IU FSH:300 IU hCG, 150 IU FSH:400 IU hCG, 200 IU FSH:1 IU hCG, 200 IU FSH:5 IU hCG, 200 IU FSH:10 IU hCG, 200 IU FSH:25 IU hCG, 200 IU FSH:50 IU hCG, 200 IU FSH:75 IU hCG, 200 IU FSH:100 IU hCG, 200 IU FSH:200 IU hCG, 200 IU FSH:300 IU hCG, and 200 IU FSH:400 IU hCG.

More preferably, the compositions contain FSH and hCG in the following ratios: 50 IU FSH:1 IU hCG, 50 IU FSH:5 IU hCG, 50 IU FSH:10 IU hCG, 50 IU FSH:25 IU hCG, 50 IU FSH:75 IU hCG, 50 IU FSH:100 IU hCG, 50 IU FSH:200 IU hCG, 50 IU FSH:300 IU hCG, 50 IU FSH:400 IU hCG, 75 IU FSH:1 IU hCG, 75 IU FSH:5 IU hCG, 75 IU FSH:10 IU hCG, 75 IU FSH:50 IU hCG, 75 IU FSH:100 IU hCG, 75 IU FSH:200 IU hCG, 75 IU FSH:300 IU hCG, 75 IU FSH:400 IU hCG, 100 IU FSH:1 IU hCG, 100 IU FSH:5 IU hCG, 100 IU FSH:10 IU hCG, 100 IU FSH:25 IU hCG, 100 IU FSH:50 IU hCG, 100 IU FSH:75 IU hCG, 100 IU FSH:100 IU hCG, 100 IU FSH:200 IU hCG, 100 IU FSH:300 IU hCG, 100 IU FSH:400 IU hCG, 150 IU FSH:1 IU hCG, 150 IU FSH:5 IU hCG, 150 IU FSH:10 IU hCG, 150 IU FSH:25 IU hCG, 150 IU FSH:75 IU hCG, 150 IU FSH:100 IU hCG, 150 IU FSH:200 IU hCG, 150 IU FSH:300 IU hCG, 150 IU FSH:400 IU hCG, 200 IU FSH:1 IU hCG, 200 IU FSH:5 IU hCG, 200 IU FSH:10 IU hCG, 200 IU FSH:25 IU hCG, 200 IU FSH:50 IU hCG, 200 IU FSH:75 IU hCG, 200 IU FSH:100 IU hCG, 200 IU FSH:200 IU hCG, 200 IU FSH:300 IU hCG, and 200 IU FSH:400 IU hCG.

In a more preferred embodiment, the composition contains 50 IU FSH:100 IU hCG, 50 IU FSH:200 IU hCG, or 50 IU FSH:400 IU hCG. These ratios are useful in treatment protocols requiring multiple administrations because more than one ampoule can be easily administered.

In another, more preferred embodiment, the composition contains 100 IU FSH:100 IU hCG, 100 IU FSH:200 IU hCG, or 100 IU FSH:400 IU hCG. These ratios allow a physician to select compositions with a higher dose of FSH. These compositions can be particularly useful at the outset of treatment where higher doses of FSH may be desired.

In a further more preferred embodiment, the composition contains 100 IU FSH:5 IU hCG, 100 IU FSH:10 IU hCG, or 100 IU FSH:25 IU hCG. Such compositions provide lower doses of hCG which can be advantageous at the onset of treatment.

Purified FSH can be obtained by any methods known in the art. FSH, as used herein, includes human-derived and recombinant FSH, FSH analogs, as well as deglycosylated, unglycosylated, and modified glycosylated forms.

Human-derived FSH can be purified by any means known in the art from natural sources such as urine, pituitary, and placenta. Procedures for isolating human-derived FSH are described in, e.g., Fevold et al. *Endocrinology* 26:999 (1940), Fraenkel-Conrat et al. *Proc. Soc. Exp. Biol. Med.* 45:627 (1940), McShan and Meyer, *J. Biol. Chem.* 135:473 (1940), Greep et al., ibid. 133:289 (1940), Li et al., *Science* 109:445

(1949), and Roos and Gemzell, CIBRA FOUNDATION STUDY GROUP, No. 22 (Little, Brown and Co., Boston, Mass., 1965).

Purified human-derived FSH is commercially available and is sold under the names Fostimon® (AMSA/IBSA), Metrodin HP® (Serono), and Bravelle (Ferring). Recombinant FSH can be obtained by any of several known means. For example, Keene et al., *J. Biol. Chem.* 26:4769 (1989), and WO 86/04589 describe expression and purification of biologically active human FSH in rodent cells.

Recominant FSH is also commercially available under the names Follistim® (Organon), Puregon® (Organon), and Gonal-F® (Serono). It can be advantageous to employ FSH isoforms that differ in the extent to which they are post-translationally modified. Due to different modifications, the isoforms exhibit differences in overall charge, degree of sialic acid (a terminal sugar) or sulfate incorporation, receptor binding affinity and plasma half-life. Chappel et al., *Endocrine Reviews* 4:179 (1983); Snyder et al. *Mol. Cell. Endocrin.* 54:115 (1987). These forms are separable from each other on the basis of their overall charge and all isoforms exhibit biological activity. Isoforms that exhibit a greater net negative charge are more heavily sialylated, exhibit a longer metabolic clearance rate and a greater biologic activity due to their extended plasma survival time.

hCG can be obtained by any means known in the art. hCG, as used herein, includes human-derived and recombinant hCG. Human-derived hCG can be purified from any appropriate source (e.g. urine, and placenta) by any method known in the art as disclosed in Zondek and Aschheim, *Klin. Wochenschr.* 7: 931 (1928), Katzman et al., ibid. 148:501 (1943), and Claesson et al, *Acta Endocrinol.* 1: 1 (1948), among others. Purified human hCG is commercially available and is sold under the names Profasi HP® (Serono), Gonasi® (AMSA/IBSA), and Choragon, Novarelin (Ferring). Methods of expressing and purifying recombinant hCG are known in the art and are disclosed, for example, in Gupta and Dighe, *J. Mol Endocrinology* 22: 273 (1999).

Recombinant hCG possesses approximately 25 times greater activity by weight as compared human-derived hCG. For example, see Chang et al. *Fertil. Steril.* 76: 67 (2001); The European Recombinant Human Chorionic Gonadotrophin Study Group, *Fertil. Steril.* 75: 1111 (2001). Thus, the amount of hCG can be adjusted accordingly to provide the desired international units of hCG activity when recombinant hCG is used in the compositions. An adjustment along this line, based on the values of FIG. 1A, is represented in FIG. 1B.

The amount of FSH and hCG activity can be determined using assay methods known in the art. 1 IU of hCG is equivalent to 5-7 IU LH in the pharmacopaeia Van Hell bioassay. Van Hell et al., *Acta Endocrin.* 47: 409 (1964). hCG activity in a composition can be determined using any assay methods known, including the Van Hell bioassay, radioreceptor assays as described, for instance, in Dighe & Moudgal. *Arch. Biochem. Biophys.* 225: 490 (1983), whole animal bioassays, ovarian ascorbic acid depletion assay, and the MA10 Leydig cell bioassay disclosed Ascoli, *Endocrinology* 108: 88 (1981). Similarly, FSH activity can be determined using receptor binding assays and whole animal bioassays.

The amount of FSH and hCG protein in a given composition can be determined by the weight of the solid compound, protein assays, such as Bradford and Lowry assays, and immunoassay techniques such as ELISA and Western blotting.

FSH:hCG compositions can be formulated by admixing, in an aqueous solution, purified FSH and hCG products, with batch-wise adjustments to achieve the desired FSH:hCG ratio, followed by sterile filtration, sterile filling, and, if desired, lyophilization. The FSH:hCG composition also can be formulated using a method, wherein purification conditions are established that yield the desired FSH:hCG ratio in the first instance (i.e., without compounding as such).

The pharmaceutical compositions of the present invention can be formulated into well known compositions for any route of drug administration, e.g., oral, rectal, parenteral (intravenous, intramuscular, or subcutaneous), intracisternal, intravaginal, intraperitoneal, local (powders, ointments or drops), or as a buccal or nasal spray. A typical composition for such purpose comprises a pharmaceutically acceptable carrier, such as aqueous solutions, non-toxic excipients, including salts, preservatives, buffers and the like, as described in REMINGTON'S PHARMACEUTICAL SCIENCES, 15th Ed. (Mack Publishing Co., 1975), at pages 1405-12 and 1461-87, and THE NATIONAL FORMULARY XIV, 14th Ed. (American Pharmaceutical Association, 1975), among others.

Examples of suitable aqueous and non-aqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate.

The compositions of the present invention also can contain additives such as but not limited to preservatives, wetting agents, emulsifying agents, and dispersing agents. Antibacterial and antifungal agents can be included to prevent growth of microbes and includes, for example, paraben, chlorobutanol, phenol sorbic acid, and the like. Furthermore, it may be desirable to include isotonic agents such as sugars, sodium chloride, and the like.

In some cases, to effect prolonged action it is desirable to slow the absorption of FSH and hCG from subcutaneous or intramuscular injection. This can be accomplished by the use of a liquid suspension of crystalline or amorphous material with poor water solubility. The rate of absorption of FSH and hCG then depends upon its rate of dissolution which, in turn, can depend upon crystal size and crystalline form. Alternatively, delayed absorption of a parenterally administered FSH and hCG combination form is accomplished by dissolving or suspending the FSH and hCG combination in an oil vehicle.

Injectable depot forms can be made by forming microencapsule matrices of the FSH and hCG combination in biodegradable polymers such as polylactide-polyglycolide. Depending upon the ratio of FSH and hCG combination to polymer and the nature of the particular polymer employed, the rate of FSH and hCG combination release can be controlled. Examples of other biodegradable polymers include poly(orthoesters) and poly(anhydrides). Depot injectable formulations are also prepared by entrapping the FSH and hCG combination in liposomes or microemulsions which are compatible with body tissues.

Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like.

Injectable formulations can be supplied as a product having pharmaceutical compositions containing either FSH or hCG suitable for administration separately or together. If administered separately, administration can be sequential. The product can be supplied in any appropriate package. For example, a product can contain a number of pre-filled syringes containing either FSH, hCG, or a combination of both FSH and hCG, the syringes packaged in a blister package or other means to maintain sterility. A product can optionally contain instructions for using the FHS and hCG formulations.

The pH and exact concentration of the various components of the pharmaceutical composition are adjusted in accordance with routine practice in this field. See GOODMAN AND GILMAN'S THE PHARMACOLOGICAL BASIS FOR THERAPEUTICS, 7th ed.

In a preferred embodiment, the compositions of the invention are supplied as compositions for parenteral administration. General methods for the preparation of the parenteral formulations are known in the art and are described in REMINGTON: THE SCIENCE AND PRACTICE OF PHARMACY, supre, at pages 780-820. The parenteral compositions can be supplied in liquid formulation or as a solid which will be mixed with a sterile injectable medium just prior to administration. In an especially preferred embodiment, the parenteral compositions are supplied in dosage unit form for ease of administration and uniformity of dosage.

"Dosage unit form" in this description refers to physically discrete units that are suited as unitary dosages for a mammalian subject to be treated, where each unit contains a predetermined quantity of active material calculated to produce the desired therapeutic effect in association with the required pharmaceutical carrier. The specification for the novel dosage unit forms of the invention are dictated by and directly dependent on the unique characteristics of the active material and the particular therapeutic effect to be achieved and the limitations inherent in the art of compounding active materials for use in mammalian subjects.

A unit dosage form can contain, for example, 50, 75, 100, 150, and 200 IU FSH in combination with 1, 5,10, 25, 50, 75, 100, 200, 300, and 400 IU hCG. Expressed in proportions, FSH and hCG each are generally present in from about 0.1 µg to about 2000 mg/ml.

Suspensions can contain rheology modifying agents such as, e.g., ethoxylated isostearyl alcohols, polyoxyethylene sorbitol and sorbitan esters, microcrystalline cellulose, aluminum metahydroxide, bentonite, agar-agar, and tragacanth, and mixtures thereof.

One of ordinary skill will appreciate that effective amounts of the FSH and hCG and the proper ratios of FSH to hCG can be determined empirically. The compositions can be administered to a subject, in need of ovarian stimulation, as pharmaceutical compositions in combination with one or more pharmaceutically acceptable excipients. It will be understood that, when administered to a human patient, the total daily usage of the agents or composition of the present invention will be decided by the attending physician within the scope of sound medical judgment. The specific therapeutically effective dose level for any particular patient will depend upon a variety of factors: the type and degree response to be achieved; activity of the specific agent or composition employed; the specific agents or composition employed; the age, body weight, general health, sex and diet of the patient; the time of administration, route of administration, and rate of excretion of the agent; the duration of the treatment, and like factors well known in the medical arts.

Use of "Single-Vial" Combinations of FSH and hCG in Ovulatory Stimulation

Based on the treatment goals, a composition with the proper FSH to hCG ratio can be selected and the composition or a series of compositions can be administered throughout the period of ovarian stimulation. The physician can initiate stimulation with one ratio and then adjust the ratios of FSH to hCG throughout the cycle. Adjustments made during treatment can be based on the timing of administration during the cycle or in response to folliculogenetic or steroidogenetic indicators, such as the number and size of follicles and patient hormone levels.

For example, in treating anovulatory females characterized by hypogonadotropic amenorrhea, compositions of the invention can be selected and administered to mimic the levels of FSH and LH activity that occur during a normal menstrual cycle. A composition with an FSH to hCG ratio of 100:5 initially would be administered daily. Starting on day six, for example, the levels of serum estradiol and follicle number and size would be monitored. Once at least two follicles greater than 12 mm and estradiol levels higher than 200 pg/mL are detected treatment will continue using a composition with an FSH to hCG ratio of 50:200 which will be administered until the final maturation parameters of at least one follicle greater than 17 mm and estradiol levels higher than 400 pg/mL are achieved. Upon reaching the final maturation parameters, ovulation will be triggered with 10,000 IU of hCG.

During COS, compositions are selected to maximize the number of large, mature follicles while minimizing the number of small, potentially dangerous follicles. A composition with an FSH to hCG ratio of 250:10 initially would be administered daily. Beginning on day six, the levels of serum estradiol and follicle number and size would be monitored. Once at least four follicles greater than 12 mm and estradiol levels higher than 600 pg/mL are detected a composition with an FSH to hCG ratio of 50:200 will be administered until the final maturation parameters of at least five follicles greater than 17 mm and estradiol levels higher than 1,500 pg/mL are achieved. Then, ovulation would be triggered with 10,000 IU of hCG.

Preliminary clinical studies demonstrate the positive effects of administering hCG prior to inducing ovulation. The results of one study are provided in Table 1. Four groups of women received 250 IU FSH per day for the first eight days of a COS cycle. Starting on approximately day nine and continuing until approximately day twelve, Group I continued receiving 250 IU FHS per day, Group II received 50 IU FSH and 100 IU hCG per day, Group III received 50 IU FSH and 200 IU hCG per day, and Group IV received 50 IU FSH and 400 IU hCG per day. Preovulatory ultrasound revealed an increase in the number of large follicles (>14 mm) for the groups receiving hCG. Moreover, nearly twice as many oocytes were retrieved following ovulation in Groups II and III, which received 100 IU hCG and 200 IU hCG per day, respectively. The fertilization rate and number of good quality embryos were similar among all groups, but the number of pregnancies was about three-fold higher for the group receiving 100 IU hCG per day than the group receiving FSH alone. This study demonstrates that the use of FSH and hCG together, in the late stages of ovulation induction, increases the number of large follicles developing, increases the number of oocytes retrieved, and can improve pregnancy rates.

The pharmaceutical compositions can be coadministered with one or more other compounds or molecules. "Coadministered" refers to simultaneous administration in the same formulation or in two different formulations.

The compositions of the invention can be administered with or following GnRH agonists and antagonists. GnRH agonists and antagonists are used for ovulation induction procedures to prevent spontaneous ovulation during gonadotropin administration. GnRH antagonist abolishes endogenous LH activity, resulting in fewer viable oocytes. Accordingly, the compositions of the invention can be administered at the commencement of treatment with GnRH antagonists to provide LH activity levels which are sufficient to stimulate follicle development and oocyte maturation.

To provide additional flexibility, the compositions of the invention can be coadministered with the currently available gonadotropin preparations, such as pure FSH, pure hCG, pure LH, and hMG preparations. For example, 1 ampoule of the FSH:hCG combination composition having FSH 75 IU and hCG 200 IU can be coadministered with 1 ampoule of highly purified FSH containing FSH 75 IU resulting administration of 150 IU of FSH and 200 IU of hCG.

FSH:hCG compositions are administered sequentially throughout ovarian stimulation. "Sequential" administration refers to a time difference of from seconds, minutes, hours or days between the administration of the compositions. Each subsequent sequential administration can be comprised of a composition with the same ratio of FSH to hCG as the previous administration or a different ratio of FSH to hCG. In a preferred embodiment, sequential administration is performed with FSH:hCG compositions that differ in the ratio of FSH to hCG. In a more preferred embodiment each succeeding composition contains a greater amount of hCG over the preceding composition in the series. In an especially preferred embodiment, the ratio of FSH to hCG is changed incrementally as shown in FIG. 2.

In the most preferred embodiment, the ratio of FSH to hCG is adjusted throughout the series in response to patient reaction to the FSH:hCG composition as indicated by folliculogenetic and steroidogenetic markers. When 2-4 intermediate follicles (12-14 mm) are formed and estradiol levels of 200-600 pg/mL are achieved, this is an indication that adequate folliculogenesis has been achieved by an FSH-rich preparation and it is appropriate to switch to an hCG-rich preparation.

Folliculogenesis and steroidogenesis should be monitored throughout ovarian stimulation by any means known in the art. Monitoring hormone levels and follicle size provides information regarding ovarian response during the treatment regimen and allows the physician to adjust the ratio of FSH to hCG during treatment. Follicle size can be determined, for example, using transvaginal pelvic ultrasonography. Follicles are categorized as large (>14 mm), intermediate (10-14 mm) or small (<10 mm). Transvaginal pelvic ultrasound can be performed frequently, for example on treatment days 0, 6, 8, 10, 12, 14, 16, 18, and 20, until preovulatory hCG administration.

The levels of estradiol can be measured using any means known in the art from any appropriate body fluid (e.g., blood, urine, and saliva), using an immunoassay or a chemiluminescence assay.

The following example illustrates the present invention. It should be understood, however, that the invention is not to be limited to the specific conditions or details described in these examples.

Controlled Ovulatory Stimulation for In Vitro Fertilization

Treatment is initiated in the mid-luteal phase of a spontaneous menstrual cycle when a GnRH agonist is administered. Ovulation induction is started 1-2 weeks later, after spontaneous menses. Alternatively, a GnRH antagonist is administered starting on the $6^{th}$ day of ovarian stimulation. Patients receive daily injections of 200 IU FSH:10 IU hCG from day 1 and continuing until the appearance of at least 4 follicles>11 mm and serum estradiol levels of >600 pg/mL. Starting on this day and until the end of treatment patients receive daily administration of 50 IU FSH:200 IU hCG.

Treatment monitoring is conducted throughout FSH:hCG administration. Each day one blood sample is drawn between 0800-0900 and serum samples are prepared in the standard fashion. Estradiol levels are determined. Transvaginal ultrasound is performed frequently during FSH:hCG treatment and until just prior to preovulatory hCG administration. Estradiol levels are monitored using chemiluminescence assays (Chiron Corp. Diagnostics ACS 180, Milan, Italy).

Upon achievement of final maturation parameters—four follicles of >14 mm and 17 β-estradiol levels of 800-1500 pg/mL—a bolus of hCG, e.g. 10,000 IU hCG is administered to trigger ovulation and oocytes are retrieved.

TABLE 1

Effects of Variable FSH:hCG Ratios on the Outcome of the Late Stages of Ovarian Stimulation for Assisted Reproduction.

|  | Group I | Group II | Group III | Group IV |
| --- | --- | --- | --- | --- |
| Target Daily rFSH Dose Until Shift | 250 | 250 | 250 | 250 |
| Target Daily rFSH Dose After Shift | NA | 50 | 50 | 50 |
| Target daily hCG Dose After Shift | NA | 100 | 200 | 400 |
| Cycles Started | 20 | 20 | 20 | 20 |
| Stimulation Cycles Completed | 15 | 18 | 17 | 17 |
| Rate (% of participants who completed stimulation cycle) | 75% | 90% | 85% | 85% |
| Responders (those who completed stimulation cycles) |  |  |  |  |
| Overall treatment duration (days) | 11.3 ± 0.4 | 12.0 ± 0.2 | 12.2 ± 0.3 | 12.1 ± 0.2 |
| FSH Administration (days) | 11.3 ± 0.4 | 8.1 ± 0.2 | 8.4 ± 0.2 | 7.8 ± 0.3 |
| hCG Administration (days) | NA | 3.9 ± 0.2 | 3.9 ± 0.2 | 4.3 ± 0.2 |
| Actual Amount rFSH Administered (total IU throughout duration of cycle) | 2833 ± 103 | 2211 ± 52 | 2297 ± 49 | 2156 ± 58 |
| Actual Amount hCG Administered (total IU throughout duration of | NA | 394 ± 21 | 776 ± 34 | 1718 ± 75 |

TABLE 1-continued

Effects of Variable FSH:hCG Ratios on the Outcome of the Late
Stages of Ovarian Stimulation for Assisted Reproduction.

|  | Group I | Group II | Group III | Group IV |
|---|---|---|---|---|
| cycle) Preovulatory Ultrasound | | | | |
| Small Follicles (<10 mm) | 5.9 ± 0.5 | 2.8 ± 0.3 | 2.4 ± 0.2 | 1.9 ± 0.1 |
| Intermediate Follicles (10-14 mm) | 6.4 ± 0.7 | 3.4 ± 0.6 | 3.2 ± 0.8 | 3.1 ± 0.4 |
| Large Follicles (>14 mm) | 7.4 ± 1.1 | 14.2 ± 1.1 | 16.7 ± 1.5 | 15.3 ± 1.6 |
| Total Follicles (per respondent) ART Results | 19.7 ± 2.0 | 20.4 ± 1.7 | 22.3 ± 2.0 | 20.3 ± 1.8 |
| Oocytes retrieved (per stimulation cycle) | 7.5 ± 1.4 | 13.2 ± 1.2 | 13.5 ± 1.7 | 9.8 ± 1.3 |
| Ferilization Rate (fertilized oocytes/oocytes retrieved) | 64 ± 7% | 64 ± 3% | 65 ± 4% | 61 ± 7 |
| Good Quality Embryos (good quality oocytes/total number embryos obtained) | 83 ± 7% | 83 ± 5% | 80 ± 5% | 73 ± 8% |
| Embryos Transferred (per stimulation cycle) | 2.0 ± 0.2 | 2.3 ± 0.1 | 2.4 ± 0.1 | 2.4 ± 0.2 |
| Positive Pregnancy Tests | 2 | 8 | 4 | 4 |
| Positive Pregnancy Test Rate (per total stimulation cycles) | 13% | 44% | 24% | 24% |
| Ultrasound Detected Pregnancies | 2 | 7 | 4 | 3 |
| Ultrasound Detected Pregnancy Rate (per total stimulation cycles) | 13% | 39% | 24% | 18% |
| Twin Gestations | 0 | 0 | 1 | 0 |
| Abortions (spontaneous) | 0 | 1 | 0 | 2 |
| Abortion Rate (per total number of pregnancies obtained) | 0% | 14% | 0% | 67% |

What is claimed is:

1. An assemblage comprising:
   (i) a first container comprising an injectable pharmaceutical composition of FSH; and
   (ii) a second container consisting essentially of an injectable pharmaceutical composition of hCG and FSH in at least one pharmaceutically acceptable carrier, wherein the amount of hCG and FSH in the second container is selected from the group consisting of: 100 IU hCG and 50 IU FSH; 200 IU hCG and 50 IU FSH; 25 IU hCG and 75 IU FSH; 50 IU hCG and 75 IU FSH; 75 IU hCG and 75 IU FSH; 100 IU hCG and 75 IU FSH; 25 IU hCG and 150 IU FSH; 50 IU hCG and 150 IU FSH; 75 IU hCG and 150 IU FSH; and 100 IU hCG and 150 IU FSH.

2. The assemblage of claim 1, wherein the amount of hCG and FSH in the second container is selected from the group consisting of: 50 IU hCG and 75 IU FSH; 50 IU hCG and 150 IU FSH; 100 IU hCG and 75 IU FSH; and 100 IU hCG and 150 IU FSH.

3. The assemblage of claim 2, wherein the amount of FSH and hCG in the second container is selected from the group consisting of 50 IU FSH and 100 IU hCG, and 50 IU FSH and 200 IU hCG.

4. The assemblage of claim 3, wherein the amount of FSH and hCG in the second container is 50 IU FSH and 100 IU hCG.

5. The assemblage of claim 1, wherein said containers are vials and said compositions are liquids.

6. The assemblage of claim 1, wherein said containers are pre-filled syringes or cartridges.

7. The assemblage of claim 1, further comprising:
   instructions to co-administer the compositions of the first and second containers.

* * * * *